(12) United States Patent
Cahalan

(10) Patent No.: US 7,033,372 B1
(45) Date of Patent: Apr. 25, 2006

(54) CORKSCREW REINFORCED LEFT VENTRICLE TO CORONARY ARTERY CHANNEL

(75) Inventor: Patrick Cahalan, Windham, NH (US)

(73) Assignee: Percardia, Inc., Merrimack, NH (US)

( * ) Notice: Subject to any disclaimer, the term of this patent is extended or adjusted under 35 U.S.C. 154(b) by 292 days.

(21) Appl. No.: 10/048,408

(22) PCT Filed: Aug. 3, 2000

(86) PCT No.: PCT/US00/21120

§ 371 (c)(1),
(2), (4) Date: Jun. 7, 2002

(87) PCT Pub. No.: WO01/10340

PCT Pub. Date: Feb. 15, 2001

Related U.S. Application Data

(60) Provisional application No. 60/147,210, filed on Aug. 4, 1999.

(51) Int. Cl.
*A61B 17/34* (2006.01)

(52) U.S. Cl. .................. 606/185; 606/167; 128/898

(58) Field of Classification Search ............... 606/185, 606/186, 213, 219, 220, 200, 167; 623/1.1–1.2; 128/898

See application file for complete search history.

(56) References Cited

U.S. PATENT DOCUMENTS

| | | | |
|---|---|---|---|
| 4,503,568 A | 3/1985 | Madras | |
| 4,733,665 A | 3/1988 | Palmaz | |
| 4,769,029 A | 9/1988 | Patel | |
| 4,953,553 A | 9/1990 | Tremulis | |
| 4,995,857 A | 2/1991 | Arnold | |
| 5,035,702 A | 7/1991 | Taherei | |
| 5,135,467 A | 8/1992 | Citron | |
| 5,193,546 A | 3/1993 | Shaknovich | |
| 5,258,008 A | 11/1993 | Wilk | |
| 5,287,861 A | 2/1994 | Wilk | |
| 5,330,486 A | 7/1994 | Wilk | |
| 5,344,426 A | 9/1994 | Lau et al. | |
| 5,385,541 A | 1/1995 | Kirsch et al. | |
| 5,389,096 A | 2/1995 | Aita et al. | |
| 5,409,019 A | 4/1995 | Wilk | |
| 5,423,744 A | 6/1995 | Gincheff et al. | |
| 5,423,851 A | 6/1995 | Samuels | |
| 5,429,144 A | 7/1995 | Wilk | |
| 5,443,497 A | 8/1995 | Venbrux | |
| 5,456,712 A | 10/1995 | Maginot | |
| 5,456,714 A | 10/1995 | Owen | |
| 5,470,320 A | 11/1995 | Tiefenbrun et al. | |
| 5,527,337 A | 6/1996 | Stack et al. | |
| 5,554,119 A | 9/1996 | Harrison et al. | |

(Continued)

FOREIGN PATENT DOCUMENTS

AU 200154153 A1 1/2002

(Continued)

OTHER PUBLICATIONS

Tweden et al., "Ventriculocoronary Artery Bypass (VCAB), a Novel Approach to Myocardial Revascularization" Feb. 2000.

(Continued)

*Primary Examiner*—Vy Q. Bui
(74) *Attorney, Agent, or Firm*—Finnegan, Henderson, Farabow, Garrett & Dunner LLP

(57) ABSTRACT

A coil is screwed into the heart wall HW between the left ventricle and coronary artery, followed by forming of a channel with laser, plasma, electrical, or mechanical device therethrough.

13 Claims, 1 Drawing Sheet

U.S. PATENT DOCUMENTS

| | | |
|---|---|---|
| 5,578,075 A | 11/1996 | Dayton |
| 5,593,434 A | 1/1997 | Williams |
| 5,609,626 A | 3/1997 | Quijano et al. |
| 5,618,299 A | 4/1997 | Khosravi et al. |
| 5,655,548 A | 8/1997 | Nelson et al. |
| 5,662,124 A | 9/1997 | Wilk .................... 128/898 |
| 5,733,267 A | 3/1998 | Del Toro |
| 5,755,682 A | 5/1998 | Knudson et al. |
| 5,758,663 A | 6/1998 | Wilk et al. |
| 5,797,933 A | 8/1998 | Snow et al. |
| 5,807,384 A | 9/1998 | Mueller |
| 5,810,836 A * | 9/1998 | Hussein et al. ............ 623/1.15 |
| 5,824,038 A | 10/1998 | Wall |
| 5,824,071 A | 10/1998 | Nelson et al. |
| 5,830,222 A | 11/1998 | Makower et al. |
| 5,843,163 A | 12/1998 | Wall |
| 5,851,232 A | 12/1998 | Lois |
| 5,855,597 A | 1/1999 | Jayaraman |
| 5,865,723 A | 2/1999 | Love |
| 5,876,373 A | 3/1999 | Giba et al. |
| 5,876,419 A | 3/1999 | Carpenter et al. |
| 5,878,751 A | 3/1999 | Hussein et al. ............ 128/898 |
| 5,885,259 A | 3/1999 | Berg |
| 5,908,028 A | 6/1999 | Wilk |
| 5,908,029 A | 6/1999 | Knudson et al. |
| 5,922,022 A | 7/1999 | Nash et al. |
| 5,925,012 A | 7/1999 | Murphy-Chutorian et al. |
| 5,931,848 A | 8/1999 | Saadat |
| 5,935,119 A | 8/1999 | Guy et al. |
| 5,935,161 A | 8/1999 | Robinson et al. |
| 5,935,162 A | 8/1999 | Dang |
| 5,938,632 A | 8/1999 | Ellis |
| 5,944,019 A | 8/1999 | Knudson et al. |
| 5,961,548 A | 10/1999 | Schmulewitz |
| 5,968,064 A | 10/1999 | Selmon et al. |
| 5,968,093 A | 10/1999 | Kranz |
| 5,971,993 A | 10/1999 | Hussein et al. |
| 5,976,155 A | 11/1999 | Foreman et al. |
| 5,976,159 A | 11/1999 | Bolduc et al. |
| 5,976,169 A | 11/1999 | Imran |
| 5,976,181 A | 11/1999 | Whelan et al. |
| 5,976,182 A | 11/1999 | Cox |
| 5,976,192 A | 11/1999 | McIntyre et al. |
| 5,976,650 A | 11/1999 | Campbell et al. |
| 5,979,455 A | 11/1999 | Maginot |
| 5,980,533 A | 11/1999 | Holman |
| 5,980,548 A * | 11/1999 | Evans et al. ................ 606/185 |
| 5,980,551 A | 11/1999 | Summers et al. |
| 5,980,552 A | 11/1999 | Pinchasik et al. |
| 5,980,553 A | 11/1999 | Gray et al. |
| 5,980,566 A | 11/1999 | Alt et al. |
| 5,984,955 A | 11/1999 | Wisselink |
| 5,984,956 A | 11/1999 | Tweden et al. |
| 5,984,963 A | 11/1999 | Ryan et al. |
| 5,984,965 A | 11/1999 | Knapp et al. |
| 5,989,207 A | 11/1999 | Hughes |
| 5,989,287 A | 11/1999 | Yang et al. |
| 5,993,481 A | 11/1999 | Marcade et al. |
| 5,993,482 A | 11/1999 | Chuter |
| 5,997,525 A | 12/1999 | March et al. |
| 5,997,563 A | 12/1999 | Kretiers |
| 5,997,573 A | 12/1999 | Quijano et al. |
| 5,999,678 A | 12/1999 | Murphy-Chutorian et al. |
| 6,001,123 A | 12/1999 | Lau |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,007,575 A | 12/1999 | Samuels |
| 6,007,576 A | 12/1999 | McClellan |
| 6,010,449 A | 1/2000 | Selmon et al. |
| 6,010,530 A | 1/2000 | Goicoechea |
| 6,017,365 A | 1/2000 | Van Oepen |
| 6,026,814 A | 2/2000 | LaFontaine et al. |
| 6,029,672 A | 2/2000 | Vanney et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,045,565 A | 4/2000 | Ellis et al. |
| 6,053,911 A | 4/2000 | Ryan et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower et al. |
| 6,071,292 A | 6/2000 | Makowen et al. |
| 6,076,529 A | 6/2000 | Vanney et al. |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |
| 6,095,997 A | 8/2000 | French et al. |
| 6,102,941 A | 8/2000 | Tweden et al. |
| 6,106,538 A | 8/2000 | Shiber |
| 6,110,201 A | 8/2000 | Quijano et al. |
| 6,113,630 A | 9/2000 | Vanney et al. |
| 6,113,823 A | 9/2000 | Eno |
| 6,117,165 A | 9/2000 | Becker |
| 6,120,520 A | 9/2000 | Saadat et al. |
| 6,123,682 A | 9/2000 | Knudson et al. |
| 6,126,649 A | 10/2000 | Van Tassel et al. |
| 6,126,654 A | 10/2000 | Giba et al. |
| 6,132,451 A | 10/2000 | Payne et al. |
| 6,139,541 A | 10/2000 | Vanney et al. |
| 6,152,141 A | 11/2000 | Stevens et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,162,245 A | 12/2000 | Jayaraman |
| 6,165,185 A | 12/2000 | Shennib et al. |
| 6,165,188 A | 12/2000 | Saadat et al. |
| 6,171,251 B1 | 1/2001 | Mueller et al. |
| 6,182,668 B1 | 2/2001 | Tweden et al. |
| 6,186,972 B1 | 2/2001 | Nelson et al. |
| 6,187,034 B1 | 2/2001 | Frantzen |
| 6,190,353 B1 | 2/2001 | Makower et al. |
| 6,193,726 B1 | 2/2001 | Vanney |
| 6,193,734 B1 | 2/2001 | Bolduc et al. |
| D438,618 S | 3/2001 | Solem |
| 6,196,230 B1 | 3/2001 | Hall et al. |
| 6,197,050 B1 | 3/2001 | Eno et al. |
| 6,197,324 B1 | 3/2001 | Crittenden |
| 6,200,311 B1 | 3/2001 | Danek et al. |
| 6,203,556 B1 | 3/2001 | Evans et al. |
| 6,213,126 B1 | 4/2001 | LaFontaine et al. |
| 6,214,041 B1 | 4/2001 | Tweden et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,245,102 B1 | 6/2001 | Jayaraman |
| 6,248,112 B1 | 6/2001 | Gambale et al. |

| | | |
|---|---|---|
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,719 B1 | 9/2001 | Garberoglio |
| 6,290,728 B1 | 9/2001 | Phelps et al. |
| 6,293,955 B1 | 9/2001 | Houser et al. |
| 6,302,875 B1 | 10/2001 | Makower et al. |
| 6,302,892 B1 | 10/2001 | Wilk |
| 6,306,125 B1 | 10/2001 | Parker et al. |
| 6,322,548 B1 | 11/2001 | Payne et al. |
| 6,330,884 B1 | 12/2001 | Kim |
| 6,344,027 B1 | 2/2002 | Goll |
| 6,350,248 B1 | 2/2002 | Knudson et al. |
| 6,352,543 B1 | 3/2002 | Cole |
| 6,361,519 B1 | 3/2002 | Knudson et al. |
| 6,363,938 B1 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B1 | 5/2002 | Wolf et al. |
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B1 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B1 | 9/2002 | Gambale et al. |
| 6,447,539 B1 | 9/2002 | Nelson et al. |
| 6,454,760 B1 | 9/2002 | Vanney |
| 6,454,794 B1 | 9/2002 | Knudson et al. |
| 6,458,092 B1 | 10/2002 | Gambale et al. |
| 6,458,140 B1 | 10/2002 | Akin et al. |
| 6,458,323 B1 | 10/2002 | Boekstegers |
| 6,464,709 B1 | 10/2002 | Shennib et al. |
| 6,475,226 B1 | 11/2002 | Belef et al. |
| 6,475,244 B1 | 11/2002 | Herweck et al. |
| 6,482,220 B1 | 11/2002 | Mueller |
| 6,491,689 B1 | 12/2002 | Ellis et al. |
| 6,491,707 B1 | 12/2002 | Makower et al. |
| 6,506,408 B1 | 1/2003 | Palasis |
| 6,508,783 B1 | 1/2003 | DeVore |
| 6,508,824 B1 | 1/2003 | Flaherty et al. |
| 6,508,825 B1 | 1/2003 | Selmon et al. |
| 6,511,458 B1 | 1/2003 | Milo et al. |
| 6,514,217 B1 | 2/2003 | Selmon et al. |
| 6,514,271 B1 | 2/2003 | Evans et al. |
| 6,517,527 B1 | 2/2003 | Gambale et al. |
| 6,517,558 B1 | 2/2003 | Gittings et al. |
| 6,524,323 B1 | 2/2003 | Nash et al. |
| 6,524,324 B1 | 2/2003 | Mueller et al. |
| 6,530,914 B1 | 3/2003 | Mickley |
| 6,533,779 B1 | 3/2003 | Kinsella et al. |
| 6,544,220 B1 | 4/2003 | Shuman et al. |
| 6,544,230 B1 | 4/2003 | Flaherty |
| 6,559,132 B1 | 5/2003 | Holmer |
| 6,561,998 B1 | 5/2003 | Roth et al. |
| 6,562,066 B1 | 5/2003 | Martin |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,573,311 B1 | 6/2003 | Martakos et al. |
| 6,575,168 B1 | 6/2003 | LaFontaine et al. |
| 6,579,311 B1 | 6/2003 | Makower |
| 6,582,444 B1 | 6/2003 | Wilk |
| 6,582,463 B1 | 6/2003 | Mowry et al. |
| 6,585,650 B1 | 7/2003 | Solem |
| 6,587,718 B1 | 7/2003 | Talpade |
| 6,589,164 B1 | 7/2003 | Flaherty |
| 6,599,304 B1 | 7/2003 | Selmon et al. |
| 6,602,241 B1 | 8/2003 | Makower et al. |
| 6,605,053 B1 | 8/2003 | Kamm et al. |
| 6,605,113 B1 | 8/2003 | Wilk |
| 6,610,100 B1 | 8/2003 | Phelps et al. |
| 6,613,026 B1 | 9/2003 | Palasis et al. |
| 6,613,081 B1 | 9/2003 | Kim et al. |
| 6,616,626 B1 | 9/2003 | Crank et al. |
| 6,616,675 B1 | 9/2003 | Evard et al. |
| 6,632,470 B1 | 10/2003 | Morra et al. |
| 6,635,214 B1 | 10/2003 | Rapacki et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B1 | 11/2003 | Wolf et al. |
| 6,651,670 B1 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,666,863 B1 | 12/2003 | Wentzel et al. |
| 6,669,691 B1 | 12/2003 | Taimisto |
| 6,669,709 B1 | 12/2003 | Cohn et al. |
| 6,676,695 B1 | 1/2004 | Solem |
| 6,685,648 B1 | 2/2004 | Flaherty et al. |
| 6,685,716 B1 | 2/2004 | Flaherty et al. |
| 6,694,983 B1 | 2/2004 | Wolf et al. |
| 6,709,425 B1 | 3/2004 | Gambale et al. |
| 6,709,427 B1 | 3/2004 | Nash et al. |
| 6,709,444 B1 | 3/2004 | Makower |
| 6,719,770 B1 | 4/2004 | Laufer et al. |
| 2001/0000041 A1 | 3/2001 | Selmon et al. |
| 2001/0003985 A1 | 6/2001 | Lafontaine et al. |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0008969 A1 | 7/2001 | Evans et al. |
| 2001/0012924 A1 | 8/2001 | Milo et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0029385 A1 | 10/2001 | Shennib et al. |
| 2001/0034547 A1 | 10/2001 | Hall et al. |
| 2001/0037117 A1 | 11/2001 | Gambale et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 | 11/2001 | Lepulu et al. |
| 2001/0044631 A1 | 11/2001 | Akin et al. |
| 2001/0047165 A1 | 11/2001 | Makower et al. |
| 2001/0047197 A1 | 11/2001 | Foley |

| | | | | | | |
|---|---|---|---|---|---|---|
| 2001/0049523 | A1 | 12/2001 | DeVore et al. | 2003/0153901 A1 | 8/2003 | Herweck et al. |
| 2001/0053932 | A1 | 12/2001 | Phelps et al. | 2003/0158509 A1 | 8/2003 | Tweden et al. |
| 2002/0002349 | A1 | 1/2002 | Flaherty et al. | 2003/0158573 A1 | 8/2003 | Gittings et al. |
| 2002/0004662 | A1 | 1/2002 | Wilk | 2003/0163198 A1 | 8/2003 | Morra et al. |
| 2002/0004663 | A1 | 1/2002 | Gittings et al. | 2003/0171800 A1 | 9/2003 | Bicek et al. |
| 2002/0007138 | A1 | 1/2002 | Wilk et al. | 2003/0181938 A1 | 9/2003 | Roth et al. |
| 2002/0029079 | A1 | 3/2002 | Kim et al. | 2003/0191449 A1 | 10/2003 | Nash et al. |
| 2002/0032476 | A1 | 3/2002 | Gambale et al. | 2003/0195457 A1 | 10/2003 | LaFontaine et al. |
| 2002/0032478 | A1 | 3/2002 | Boeksteggers et al. | 2003/0195458 A1 | 10/2003 | Phelps et al. |
| 2002/0033180 | A1 | 3/2002 | Solem | 2003/0195606 A1 | 10/2003 | Davidson et al. |
| 2002/0045928 | A1 | 4/2002 | Boekstegers | 2003/0204160 A1 | 10/2003 | Kamm et al. |
| 2002/0049486 | A1 | 4/2002 | Knudson et al. | 2003/0212413 A1 | 11/2003 | Wilk |
| 2002/0049495 | A1 | 4/2002 | Kutryk et al. | 2003/0216678 A1 | 11/2003 | March et al. |
| 2002/0058897 | A1 | 5/2002 | Renati | 2003/0216679 A1 | 11/2003 | Wolf et al. |
| 2002/0062146 | A1 | 5/2002 | Makower et al. | 2003/0216801 A1 | 11/2003 | Tweden et al. |
| 2002/0065478 | A1 | 5/2002 | Knudson et al. | 2003/0220661 A1 | 11/2003 | Mowry et al. |
| 2002/0072699 | A1 | 6/2002 | Knudson et al. | 2003/0225425 A1 | 12/2003 | Kupiecki et al. |
| 2002/0072758 | A1 | 6/2002 | Reo et al. | 2003/0229366 A1 | 12/2003 | Reggie et al. |
| 2002/0077566 | A1 | 6/2002 | Laroya et al. | 2003/0236542 A1 | 12/2003 | Makower |
| 2002/0077654 | A1 | 6/2002 | Javier, Jr. et al. | 2004/0006298 A1 | 1/2004 | Wilk |
| 2002/0082546 | A1 | 6/2002 | Crank et al. | 2004/0006301 A1 | 1/2004 | Sell et al. |
| 2002/0092535 | A1 | 7/2002 | Wilk | 2004/0015193 A1 | 1/2004 | Lamson et al. |
| 2002/0092536 | A1 | 7/2002 | LaFontaine et al. | 2004/0015225 A1 | 1/2004 | Kim et al. |
| 2002/0095110 | A1 | 7/2002 | Vanney et al. | 2004/0019348 A1 | 1/2004 | Stevens et al. |
| 2002/0095111 | A1 | 7/2002 | Tweden et al. | 2004/0037946 A1 | 2/2004 | Morra et al. |
| 2002/0095206 | A1 | 7/2002 | Addonizio et al. | 2004/0044392 A1 | 3/2004 | Von Oepen |
| 2002/0099392 | A1 | 7/2002 | Mowry et al. | 2004/0059280 A1 | 3/2004 | Makower et al. |
| 2002/0099404 | A1 | 7/2002 | Mowry | 2004/0073157 A1 | 4/2004 | Knudson et al. |
| 2002/0100484 | A1 | 8/2002 | Hall et al. | 2004/0073238 A1 | 4/2004 | Makower |
| 2002/0103459 | A1 | 8/2002 | Sparks et al. | 2004/0077987 A1 | 4/2004 | Rapacki et al. |
| 2002/0103495 | A1 | 8/2002 | Cole | 2004/0077988 A1 | 4/2004 | Tweden et al. |
| 2002/0103534 | A1 | 8/2002 | Vanney et al. | 2004/0077990 A1 | 4/2004 | Knudson et al. |
| 2002/0111644 | A1 | 8/2002 | Shuman et al. | 2004/0092976 A1 | 5/2004 | Mowry et al. |
| 2002/0111672 | A1 | 8/2002 | Kim et al. | | | |
| 2002/0123698 | A1 | 9/2002 | Garibotto et al. | FOREIGN PATENT DOCUMENTS | | |
| 2002/0123786 | A1 | 9/2002 | Gittings et al. | | | |
| 2002/0138087 | A1 | 9/2002 | Shennib et al. | AU | 757647 | 2/2003 |
| 2002/0143285 | A1 | 10/2002 | Eno et al. | EP | 0 732 088 A2 | 9/1996 |
| 2002/0143289 | A1 | 10/2002 | Ellis et al. | EP | 0 815 798 A2 | 7/1997 |
| 2002/0143347 | A1 | 10/2002 | Cole et al. | EP | 0 829 239 A1 | 8/1997 |
| 2002/0144696 | A1 | 10/2002 | Sharkawy et al. | EP | 0 792 624 A1 | 9/1997 |
| 2002/0161383 | A1 | 10/2002 | Akin et al. | EP | 0 797 957 A1 | 10/1997 |
| 2002/0161424 | A1 | 10/2002 | Rapacki et al. | EP | 0 797 958 A1 | 10/1997 |
| 2002/0165479 | A1 | 11/2002 | Wilk | EP | 0 799 604 A1 | 10/1997 |
| 2002/0165606 | A1 | 11/2002 | Wolf et al. | EP | 0 801 928 A1 | 10/1997 |
| 2002/0179098 | A1 | 12/2002 | Makower et al. | EP | 0 836 834 A2 | 10/1997 |
| 2002/0183716 | A1 | 12/2002 | Herweck et al. | EP | 0 824 903 A1 | 2/1998 |
| 2002/0193782 | A1 | 12/2002 | Ellis et al. | EP | 0 876 796 A2 | 5/1998 |
| 2003/0015816 | A1 | 1/2003 | Rapacki et al. | EP | 0 853 921 A2 | 7/1998 |
| 2003/0018379 | A1 | 1/2003 | Knudson et al. | EP | 0 858 779 A1 | 8/1998 |
| 2003/0036698 | A1 | 2/2003 | Kohler et al. | EP | 0 876 803 A2 | 11/1998 |
| 2003/0044315 | A1 | 3/2003 | Boekstegers | EP | 0 888 750 A1 | 1/1999 |
| 2003/0045828 | A1 | 3/2003 | Wilk | EP | 0 895 752 A2 | 2/1999 |
| 2003/0055371 | A1 | 3/2003 | Wolf et al. | EP | 0 903 123 A1 | 3/1999 |
| 2003/0062650 | A1 | 4/2003 | Martakos et al. | EP | 0 904 745 A2 | 3/1999 |
| 2003/0069532 | A1 | 4/2003 | Mowry et al. | EP | 0 934 728 A2 | 8/1999 |
| 2003/0069587 | A1 | 4/2003 | Schorgl et al. | EP | 0 955 017 A2 | 11/1999 |
| 2003/0073973 | A1 | 4/2003 | Evans et al. | EP | 0 955 019 A2 | 11/1999 |
| 2003/0074006 | A1 | 4/2003 | Mowry et al. | EP | 0 962 194 A2 | 12/1999 |
| 2003/0078561 | A1 | 4/2003 | Gambale et al. | EP | 1 020 166 A1 | 7/2000 |
| 2003/0078562 | A1 | 4/2003 | Makower et al. | EP | 1 027 870 A1 | 8/2000 |
| 2003/0083678 | A1 | 5/2003 | Herweck et al. | EP | 1 088 564 A1 | 4/2001 |
| 2003/0097172 | A1 | 5/2003 | Shalev et al. | EP | 1 097 676 A1 | 5/2001 |
| 2003/0100920 | A1 | 5/2003 | Akin et al. | EP | 1 166 721 A2 | 1/2002 |
| 2003/0105514 | A1 | 6/2003 | Phelps et al. | EP | 0 959 815 A1 | 12/2002 |
| 2003/0114872 | A1 | 6/2003 | Mueller et al. | EP | 1 112 097 A1 | 6/2003 |
| 2003/0120195 | A1 | 6/2003 | Milo et al. | GB | 2316322 | 10/1998 |
| 2003/0120259 | A1 | 6/2003 | Mickley | WO | WO 94/16629 | 8/1994 |
| 2003/0125798 | A1 | 7/2003 | Martin | WO | WO 96/32972 | 10/1996 |
| 2003/0130611 | A1 | 7/2003 | Martin | WO | WO 96/35469 | 11/1996 |
| 2003/0130719 | A1 | 7/2003 | Martin | WO | WO 96/39962 | 12/1996 |
| 2003/0135260 | A1 | 7/2003 | Kohler et al. | WO | WO 96/39964 | 12/1996 |
| 2003/0149474 | A1 | 8/2003 | Becker | WO | WO 96/39965 | 12/1996 |

| | | | | | |
|---|---|---|---|---|---|
| WO | 97/13463 | 4/1997 | WO | 00/15149 | 3/2000 |
| WO | 97/13471 | 4/1997 | WO | 00/15275 | 3/2000 |
| WO | WO 97/18768 | 5/1997 | WO | WO 00/10623 | 3/2000 |
| WO | 97/27893 | 8/1997 | WO | WO 00/13722 | 3/2000 |
| WO | 97/27897 | 8/1997 | WO | 00/21436 | 4/2000 |
| WO | 97/27898 | 8/1997 | WO | 00/21461 | 4/2000 |
| WO | 97/32551 | 9/1997 | WO | 00/21463 | 4/2000 |
| WO | WO 97/41916 | 11/1997 | WO | WO 00/18302 | 4/2000 |
| WO | WO 97/43961 | 11/1997 | WO | WO 00/18323 | 4/2000 |
| WO | WO 98/02099 | 1/1998 | WO | WO 00/18325 | 4/2000 |
| WO | WO 98/03118 | 1/1998 | WO | WO 00/18326 | 4/2000 |
| WO | 98/06356 | 2/1998 | WO | WO 00/18331 | 4/2000 |
| WO | WO 98/06356 | 2/1998 | WO | WO 00/18462 | 4/2000 |
| WO | 98/08456 | 3/1998 | WO | 00/24449 | 5/2000 |
| WO | 98/10714 | 3/1998 | WO | 00/33725 | 6/2000 |
| WO | 98/16161 | 4/1998 | WO | WO 00/35376 | 6/2000 |
| WO | WO 98/19607 | 5/1998 | WO | WO 00/36997 | 6/2000 |
| WO | WO 98/24373 | 6/1998 | WO | 00/41632 | 7/2000 |
| WO | WO 98/25533 | 6/1998 | WO | 00/41633 | 7/2000 |
| WO | WO 98/38916 | 9/1998 | WO | WO 00/43051 | 7/2000 |
| WO | WO 98/38925 | 9/1998 | WO | 00/45711 | 8/2000 |
| WO | WO 98/38939 | 9/1998 | WO | WO 00/45886 | 8/2000 |
| WO | WO 98/38941 | 9/1998 | WO | WO 00/49952 | 8/2000 |
| WO | WO 98/39038 | 9/1998 | WO | WO 00/49954 | 8/2000 |
| WO | 98/46115 | 10/1998 | WO | WO 00/49956 | 8/2000 |
| WO | 98/46119 | 10/1998 | WO | 00/56387 | 9/2000 |
| WO | WO 98/44869 | 10/1998 | WO | WO 00/54660 | 9/2000 |
| WO | WO 98/49964 | 11/1998 | WO | WO 00/54661 | 9/2000 |
| WO | WO 98/53759 | 12/1998 | WO | WO 00/56224 | 9/2000 |
| WO | WO 98/55027 | 12/1998 | WO | WO 00/56225 | 9/2000 |
| WO | WO 98/57590 | 12/1998 | WO | 00/66007 | 11/2000 |
| WO | WO 98/57591 | 12/1998 | WO | 00/66009 | 11/2000 |
| WO | WO 98/57592 | 12/1998 | WO | 00/66035 | 11/2000 |
| WO | 99/08624 | 2/1999 | WO | 00/71195 A1 | 11/2000 |
| WO | WO 99/07296 | 2/1999 | WO | WO 00/69345 | 11/2000 |
| WO | 99/17683 | 4/1999 | WO | WO 00/69504 | 11/2000 |
| WO | WO 99/15220 | 4/1999 | WO | 01/10340 A1 | 2/2001 |
| WO | WO 99/17671 | 4/1999 | WO | 01/10341 A2 | 2/2001 |
| WO | 99/21490 | 5/1999 | WO | 01/10347 A1 | 2/2001 |
| WO | 99/25273 | 5/1999 | WO | 01/10348 A1 | 2/2001 |
| WO | WO 99/21510 | 5/1999 | WO | 01/10349 A1 | 2/2001 |
| WO | WO 99/22655 | 5/1999 | WO | WO 01/08566 A1 | 2/2001 |
| WO | WO 99/22658 | 5/1999 | WO | WO 01/08602 A1 | 2/2001 |
| WO | WO 99/27985 | 6/1999 | WO | WO 01/10350 A1 | 2/2001 |
| WO | 99/36000 | 7/1999 | WO | WO 01/17440 A1 | 3/2001 |
| WO | 99/36001 | 7/1999 | WO | WO 01/17456 A1 | 3/2001 |
| WO | WO 99/32051 | 7/1999 | WO | WO 01/23016 A1 | 4/2001 |
| WO | WO 99/35977 | 7/1999 | WO | WO 01/26562 A1 | 4/2001 |
| WO | WO 99/35979 | 7/1999 | WO | WO 01/41657 A1 | 6/2001 |
| WO | WO 99/35980 | 7/1999 | WO | WO 01/49187 A1 | 7/2001 |
| WO | WO 99/37218 | 7/1999 | WO | WO 01/54625 A1 | 8/2001 |
| WO | 99/38459 | 8/1999 | WO | WO 01/68158 A1 | 9/2001 |
| WO | 99/40868 | 8/1999 | WO | WO 01/70133 A2 | 9/2001 |
| WO | WO 99/40853 | 8/1999 | WO | WO 01/72239 A2 | 10/2001 |
| WO | WO 99/40963 | 8/1999 | WO | WO 01/78801 A2 | 10/2001 |
| WO | 99/48545 | 9/1999 | WO | WO 01/82803 A1 | 11/2001 |
| WO | WO 99/44524 | 9/1999 | WO | WO 01/82837 A2 | 11/2001 |
| WO | WO 99/47071 | 9/1999 | WO | WO 02/02163 A2 | 1/2002 |
| WO | WO 99/47078 | 9/1999 | WO | WO 02/011647 A2 | 2/2002 |
| WO | WO 99/48427 | 9/1999 | WO | WO 02/011807 A2 | 2/2002 |
| WO | WO 99/48549 | 9/1999 | WO | WO 02/013698 A1 | 2/2002 |
| WO | 99/49793 | 10/1999 | WO | WO 02/013699 A1 | 2/2002 |
| WO | 99/49910 | 10/1999 | WO | WO 02/013703 A1 | 2/2002 |
| WO | 99/51162 | 10/1999 | WO | WO 02/013704 A1 | 2/2002 |
| WO | 99/53863 | 10/1999 | WO | WO 02/24108 A2 | 3/2002 |
| WO | WO 99/55406 | 11/1999 | WO | WO 02/24247 A1 | 3/2002 |
| WO | 99/60941 | 12/1999 | WO | WO 02/024248 A1 | 3/2002 |
| WO | 99/62430 | 12/1999 | WO | WO 02/026310 A1 | 4/2002 |
| WO | 00/09195 | 2/2000 | WO | WO 02/026462 A1 | 4/2002 |
| WO | 00/12029 | 3/2000 | WO | WO 02/030325 A2 | 4/2002 |
| WO | 00/15146 | 3/2000 | WO | WO 02/030326 A2 | 4/2002 |
| WO | 00/15147 | 3/2000 | WO | WO 02/030330 A2 | 4/2002 |
| WO | 00/15148 | 3/2000 | WO | WO 02/032330 A2 | 4/2002 |

| WO | WO 02/034323 A2 | 5/2002 |
| WO | WO 02/045598 A2 | 6/2002 |
| WO | WO 02/049695 A2 | 6/2002 |
| WO | WO 02/056937 A2 | 7/2002 |
| WO | WO 02/058567 A2 | 8/2002 |
| WO | WO 02/058591 A2 | 8/2002 |
| WO | WO 02/060509 A1 | 8/2002 |
| WO | WO 02/062265 A2 | 8/2002 |
| WO | WO 02/064020 A2 | 8/2002 |
| WO | WO 02/071974 A2 | 9/2002 |
| WO | WO 02/074175 A2 | 9/2002 |
| WO | WO 02/091958 A1 | 11/2002 |
| WO | WO 03/008005 A2 | 1/2003 |
| WO | WO 03/015638 A2 | 2/2003 |
| WO | WO 03/017870 A1 | 3/2003 |
| WO | WO 03/024307 A2 | 3/2003 |
| WO | WO 03/028522 A2 | 4/2003 |
| WO | WO 03/030744 A1 | 4/2003 |
| WO | WO 03/030784 A1 | 4/2003 |
| WO | WO 03/079932 A2 | 10/2003 |
| WO | WO 2004/000170 A1 | 12/2003 |

OTHER PUBLICATIONS

*American Medical Association Publication;* "Myocardial Revascularization Experiments Using the Epicardium," B. G. Lary, M.D., et al.; *Archives of Surgery,* pp. 69-72, vol. 98, No. 1, Jan. 1969.
*The Journal of Thoracic and Cardiovascular Surgery,* "Experimental Evaluation of Direct Transventricular Revascularization," L. Kuzela, M.D., et al., pp. 770-773, vol. 57, Jan.-Jun. 1969, The C.V. Mosby Co., St. Louis, MO.
*The Journal of Thoracic and Cardiovascular Surgery,* "Myocardial Revascularization by a New Method of Carrying Blood Directly from the Left Ventricular Cavity into the Coronary Circulation," C Massimo, M.D., et al., pp. 257-264, Aug. 1957.
*The Journal of Thoracic and Cardiovascular Surgery,* "Experimental Evaluation of Myocardial Tunnelization as a Method of Myocardial Revascularization," I. Anabtawi, M.D., et al., pp. 638-646., Nov. 1969.
*The Journal of Thoracic and Cardiovascular Surgery,* "The Possibility of Myocardial Revascularization by Creation of a Left Ventriculocoronary Artery Fistula," I. Munro, M.D., et al., pp. 25-32., vol. 58, 1969.
*AJR,* "Expandable Inrahepatic Portacaval Shunt Stents in Dogs with Chronic Portal Hypertension," J. Palmaz, et al., pp. 1251-1256, Dec., 1988.
*AJR,* "Expandable Intrahepatic Portacaval Shunt Stents: Early Experience in the Dog," J. Palmaz, et al., pp. 821-825.
*American Heart Journal,* "Effects of Laser Irradiation Delivered by Flexible Fiberoptic System on the Left Ventricular Internal Myocardium," G. Lee, M.D., et al., pp. 587-590, vol. 106, No. 3, Sep. 1983.
*Texas Heart Institute Journal,* "Transmyocardial Laser Revascularization," D. Cooley, M.D., et al., pp. 220-224, vol. 21, No. 3, 1994.
*American Journal of Physiology,* "Transmural Myocardial Perfusion During Restricted Coronary Inflow in the Awake Dog," R. Bache, et al., pp. H645-651, vol. 232, No. 6 ISSN-0002-9513.
*The Annals of Thoracic Surgery,* "Myocardial Canalization," A. Khazei, M.D., et al., vol. 6, No. 2, Aug. 1968, pp. 163-171.
*Surgical Forum,* "Proceedings of the 24th Annual Sessions of the Forum on Fundamental Surgical Problems," 54th Clinical Congress of the American College of Surgeons, Chicago, Illinois, Oct. 1968, pp. 156-159, American College of Surgeons, Chicago, Illinois.
*Journal of Surgical Research,* "An Experimental Anatomic Study of Indirect Myocardial Revascularization," R. Gardner, M.D., et al., vol. 11, No. 5, May 1971, pp. 243-247.
*Medical Industry Today,* "Eclipse Gets OK to Pump Catheter Marketing in Europe", Jul. 1998, 2 pages.
*Medical Industry Today,* "Sales Dive, Losses Soar in 2Q for CardioGenesis", Jul. 1998, 2 pages.
US 6,331,185, 12/2001, Gambale et al. (withdrawn)

* cited by examiner

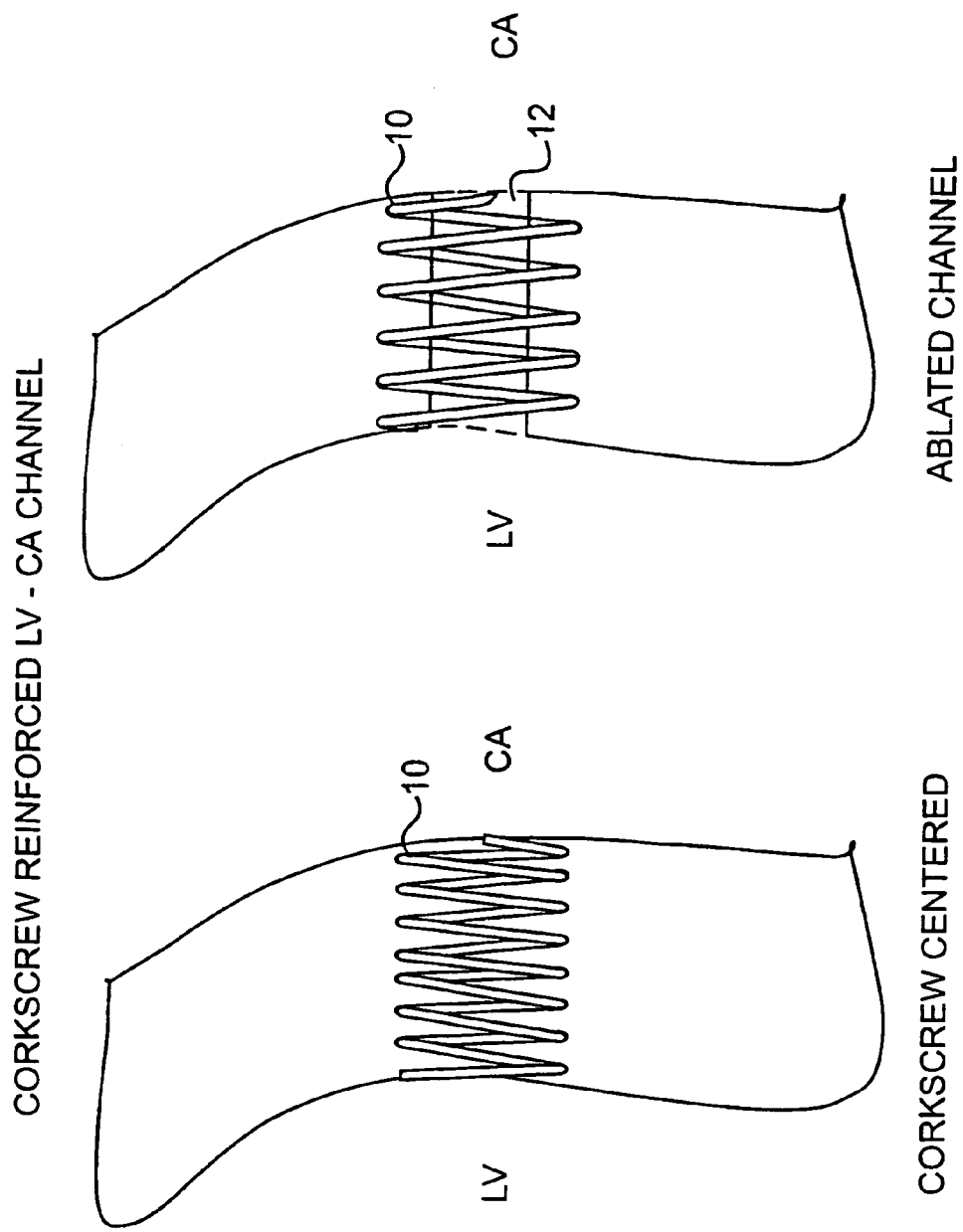

CORKSCREW REINFORCED LEFT VENTRICLE TO CORONARY ARTERY CHANNEL

CROSS REFERENCE TO RELATED APPLICATIONS

The application is a national phase application based on PCT/US00/21120, filed Aug. 3, 2000, and claims the benefit of U.S. Provisional Application No. 60/147,210, filed Aug. 4, 1999, the content of both of which is incorporated herein by reference.

BACKGROUND OF THE INVENTION

1. Field of the Invention

This invention relates to method and apparatus for forming a channel to allow communication of fluids from one portion of a patient's body to another, and more particularly, to a device that can communicate blood between the left ventricle and coronary arteries or veins.

2. Description of the Related Art

Currently there exists a shunting concept that establishes a passage from the left ventricle directly to the coronary artery by the placement of a stent or hollow tube in a channel formed therethrough. Other designs also suggested that it might be possible to have a stent-less channel (see U.S. Pat. No. 5,662,124). Both designs have to deal with problems arising from the contraction and multidimensional movements of the heart wall in relation to the device. For a straight hollow tube the movement may create irritation between the tissue and the metal interface that may lead to a chronic inflammatory response, and maybe even to dislodgement of the tube. For a collapsible or expandable "wire" stent the constant movement can lead to fracture from cyclic fatigue (this has been documented in vivo humans —by Stent Medtronic). With respect to blood compatibility a solid tube presents maximum foreign surface to the blood of materials that are all relatively thrombogenic. While a wire or open stent design has less surface area exposed to blood, the profile of the stent in the flow field is less optimal and requires optimal placement.

SUMMARY OF THE INVENTION

What is primarily needed is a device that can control the shape of the open channel between the left ventricle and coronary artery, and can withstand long and continuous complex movement without causing irritation, dislodgement, or fracture. An alternative approach to spikes, and stents, is the use of a screw in coil. The design of such a coil would be much like that of a corkscrew. This same design has been used on implantable pacemaker leads for years to anchor the electrode tips into the endocardium of the heart. This design yields very high stability in terms of pull out force and survival against mechanical dislodgement. It is also well tolerated without chronic inflammatory responses. Another advantage is in placement of the device, as it can be removed with ease and without significant tissue trauma should the initial placement attempt be less than optimal.

BRIEF DESCRIPTION OF THE DRAWINGS

FIG. 1 illustrates a partial cross-sectional view of a coil screwed into the heart wall between the left ventricle and coronary artery.

FIG. 2 illustrates a partial cross-sectional view of a channel formed through the coil of FIG. 1.

DETAILED DESCRIPTION OF THE PREFERRED EMBODIMENT

FIGS. 1 and 2 roughly show the preferred design, which would comprise first screwing in a coil 10 into the heart wall HW between the left ventricle LV and coronary artery CA (FIG. 1), and then followed by forming of a channel 12 by, for example, laser, plasma, electrical, or mechanical device (FIG. 2). At this time it would be preferred to use the plasma ablation technique as the diameter of the channel can be controlled with considerable accuracy at the dimensions one would want, and also the asymmetry can be controlled.

In one embodiment, the corkscrew or coil 10 may be configured to have a desired pitch and spacing so that insertion of the coil 10 into the heart wall does not puncture through the coronary artery CA. This is accomplished by choosing an entry point for the coil 10 adjacent the coronary artery, and screwing the coil 10 into the heart wall such that the coronary artery is positioned in between the turns of the coil as the coil is inserted. In this embodiment, the spacing between the turns of the coil is greater than the diameter of the coronary artery.

Up until now it has been suggested that blood exposure to non endothelialized tissue surfaces would be a problem for a formed, stentless channel. In reality the challenge of the denatured proteins on the surface of a formed channel is certainly no more than that of a metal surface of a tube or stent concept.

It is further envisioned that the channel formed would be optimal for "paving" with a biocompatible polymer such as a PEG macromer (Focal of MA), and this could be a rapid and catheter-based method of in situ modification of the channel to improve blood compatibility.

It is also conceivable that the "corkscrew" can be placed on the distal tip of a catheter and also serves as a guide for the subsequent forming device to make the channel. Electrical circuits can be designed to operate within defined distances from the corkscrew, and can control the forming device that requires energy sources.

An additional advantage of the corkscrew is that a slight projection into the ventricle would not create dead spots for blood pooling like that of a hollow tube. It also would not be subject to rapid over insertion as is the case with puncture like devices.

Finally the corkscrew is not actually inside the channel and therefore presents no problems of profile and placement, as would be the case with an expanding stent design. The latter variable has been thought to be the most critical parameter in intravascular stent use.

It will be appreciated that although the above embodiments have been described as being used between the coronary artery and left ventricle, the methods and apparatus described above can be used between any heart chamber and blood vessel, or through any other body tissue between two body lumens in which a channel of blood is desired to be formed.

The embodiments illustrated and described above are provided merely as examples of certain preferred embodiments of the present invention. Various changes and modifications can be made from the embodiments presented herein by those skilled in the art without departure from the spirit and scope of the invention, as defined by the appended claims.

What is claimed is:

1. A method for forming a channel between a heart chamber and a coronary vessel through body tissue, comprising:

screwing a coil into the body tissue between the heart chamber and coronary vessel; and forming a channel within the coil in the body tissue that connects the heart chamber to the coronary vessel so as to place the heart chamber and the coronary vessel in flow communication with each other, wherein the channel does not include a naturally occurring blood containing anatomical conduit, wherein the screwing of the coil into the body tissue is completed prior to the forming of the channel.

2. The method of claim 1, wherein the forming of the channel includes forming the channel via one of a laser device, a plasma ablation device, an electrical device, and a mechanical device.

3. The method of claim 1, wherein the heart chamber is a left ventricle and the body tissue is a heart wall.

4. The method of claim 3, wherein the coronary vessel is a coronary artery.

5. The method of claim 1, further comprising applying a biocompatible material to the channel.

6. The method of claim 1, further comprising screwing in the coil via a catheter.

7. A method for forming a channel between a first body lumen and a second body lumen through body tissue, comprising:

screwing a coil into the body tissue between the first and second body lumens; and forming a channel in the body tissue that connects the first body lumen to the second body lumen, the body tissue defining a lumen of the channel, wherein the coil is not within the lumen of the channel and the lumen of the channel is within the coil.

8. The method of claim 7, wherein the forming of the channel includes forming the channel via one of a laser device, a plasma ablation device, an electrical device, and a mechanical device.

9. The method of claim 7, wherein the first body lumen is a heart chamber, the second body lumen is a coronary vessel, and the body tissue is a heart wall.

10. The method of claim 9, wherein the heart chamber is a left ventricle and the coronary vessel is a coronary artery.

11. The method of claim 7, further comprising applying a biocompatible material to the channel.

12. The method of claim 7, further comprising screwing in the coil via a catheter.

13. The method of claim 7, wherein the screwing of the coil into the body tissue occurs prior to forming the channel.

* * * * *